United States Patent [19]

Onda et al.

[11] 4,226,981
[45] Oct. 7, 1980

[54] ETHER-ESTER DERIVATIVES OF CELLULOSE AND THEIR APPLICATIONS

[75] Inventors: Yoshiro Onda, Niigata; Hiroaki Muto; Kazumasa Maruyama, both of Joetsu, all of Japan

[73] Assignee: Shin-Etsu Chemical Co., Ltd., Japan

[21] Appl. No.: 944,177

[22] Filed: Sep. 20, 1978

[30] Foreign Application Priority Data

Sep. 28, 1977 [JP] Japan ................. 52/116328
Oct. 17, 1977 [JP] Japan ................. 52/124237
Oct. 25, 1977 [JP] Japan ................. 52/127947

[51] Int. Cl.² ............... B44D 1/50; C08B 13/00; G03C 1/92
[52] U.S. Cl. ............... 536/66; 424/35; 427/3; 536/65; 430/516
[58] Field of Search ............ 536/65, 66; 424/35; 427/3; 96/84 R

[56] References Cited

U.S. PATENT DOCUMENTS

| | | | |
|---|---|---|---|
| 1,994,038 | 3/1935 | Hagedorn et al. ............ | 536/66 |
| 2,759,925 | 8/1956 | Hiatt et al. ............ | 536/66 |
| 2,852,508 | 9/1958 | Hiatt et al. ............ | 536/66 |
| 2,856,399 | 10/1958 | Mench et al. ............ | 536/66 |
| 3,008,953 | 11/1961 | Crane ............ | 536/66 |
| 3,629,237 | 12/1971 | Koyanagi et al. ............ | 536/66 |
| 3,712,886 | 1/1973 | Koyanagi et al. ............ | 536/66 |
| 3,854,950 | 12/1974 | Held ............ | 96/84 R |
| 3,870,702 | 3/1975 | Koyanagi et al. ............ | 536/66 |
| 3,892,575 | 7/1975 | Watts et al. ............ | 96/84 R |
| 4,039,333 | 8/1977 | Shinagawa et al. ............ | 96/84 R |

*Primary Examiner*—Ronald W. Griffin
*Attorney, Agent, or Firm*—McGlew and Tuttle

[57] ABSTRACT

A novel cellulose derivative provided in this invention is a mixed ester of an alkoxy or hydroxyalkoxy substituted cellulose ether, prepared by the esterification reaction of the ether with succinic anhydride and an anhydride of an aliphatic monocarboxylic acid. The cellulose derivatives are advantageous because of their capability of producing enteric coatings having sufficient flexibility without the use of a plasticizer as well as by their chemical and physical stability against moisture, and also by easy purification after completion of the esterification reaction. The coatings produced from the derivatives have a similar chemical and physical stability. The cellulose derivatives are useful for the enteric coating of pharmaceutical dosage forms and also for providing halation-preventing layers on photographic films.

18 Claims, 3 Drawing Figures

ETHER-ESTER DERIVATIVES OF CELLULOSE AND THEIR APPLICATIONS

BACKGROUND OF THE INVENTION

The present invention relates to a novel class of cellulose derivatives which are mixed esters of a cellulose ether with acidic succinyl groups and aliphatic monoacyl groups, and to the enteric coating of pharmaceutical solid dosage forms of said cellulose derivatives and the prevention of halation on photographic films for which the cellulose derivatives are used.

Various known esters of cellulose per se or cellulose ethers with a carboxylic acid are useful for enteric coating and these include cellulose acetate phthalate, cellulose acetate succinate, methylcellulose phthalate, hydroxypropylmethylcellulose phthalate, methylcellulose succinate, hydroxypropylmethylcellulose succinate, and the like.

These cellulose derivatives can be used to form protective coatings on pharmaceutical solid dosage forms, particularly enterosoluble coatings, which do not dissolve in the gastric juice but readily dissolve in the intestinal juice.

However, the coating materials and enterosoluble coatings or enteric coatings produced therewith in the prior art have been found to be deficient in the following physiological inactivity to the human body, impossibility of producing toxic substances by decomposition, chemical or physical stability after the lapse of time, water resistance, i.e. stability against hydrolysis, or flexibility.

For example, cellulose acetate phthalate and cellulose acetate succinate in the powdered form or in the coating form are liable to decomposition by moisture, gradually liberating acetic acid, phthalic acid or succinic acid. Such decomposition taking place on the coated solid dosage forms results in a remarkable reduction of enterosolubility.

Further, methylcellulose phthalate and hydroxypropylmethylcellulose phthalate are defective in their flexibility as the coating material, and usually mixed with a large amount of a plasticizer. The use of plasticizers, on the other hand, brings about changes in the properties of the coatings formed due to migration of the plasticizer toward the surface of the coatings or gradual loss of the plasticizer by evaporation from the surface of the coatings with the lapse of time.

Furthermore, methylcellulose succinate and hydroxypropylcellulose succinate are free from the problem of insufficient flexibility of coatings and the disadvantageous use of plasticizers, but they are defective in that the coatings formed by these succinate derivatives adhere to each other. Additionally, the succinate derivatives tend to form lumps in the manufacturing process, especially, when the reaction product after completion of the esterification reaction is separated from the reaction mixture, thus bringing about difficulties in the purification of the reaction product.

Turning to halation prevention in photographic materials, photographic films and dry plates are invariably provided with a halation preventing layer containing colloidal carbon, graphite, dyestuffs and the like on the opposite surface of the layer of the photosensitive silver halide emulsion.

The coating compositions for providing the halation preventing layer contain a vehicle resin to act as a binder. Known vehicle resins are, by way of exemplification, copolymers of an ethylenically unsaturated carboxylic acid, such as acrylic acid-acrylic ester copolymers, and acrylonitrilemaleic anhydride copolymers; and cellulose derivatives, such as phthalates, tetrahydrophthalates, and hexahydrophthalates of a hydroxyalkylalkylcellulose, e.g. hydroxypropylmethylcellulose.

Among the above vehicle resins for the halation preventing layers, the copolymers of the unsaturated carboxylic acids are defective due to their limited solubility in organic solvents and in alkaline aqueous media, so that workability in the process of forming the halation preventing layer is relatively low and the removal or dissolution of the layer from the film substrate in the subsequent development process is effected only slowly.

Further, the above cellulose derivatives are not capable of producing coatings having sufficient flexibility and, accordingly, the photographic films provided with the halation preventing layers of the same cellulose derivatives are short of flexibility. Moreover, the cellulose derivatives themselves tend to be hydrolyzed in a humid atmosphere to form free acids, such as acetic acid, phthalic acid, tetrahydrophthalic acid, and hexahydrophthalic acid, resulting in degradating the halation preventing layers in the long run or adversely affecting the performance of photosensitive silver halide emulsion layers.

SUMMARY OF THE INVENTION

The present invention has been completed as a result of extensive investigations in order to solve the abovedescribed problems in the prior art. The invention provides a novel cellulose derivative which is a mixed ester of a cellulose ether having acidic succinyl groups and aliphatic monoacyl groups prepared by reacting a cellulose ether having alkoxy and/or hydroxyalkoxy groups with succinic anhydride and an anhydride of an aliphatic monocarboxylic acid.

The present invention also provides a pharmaceutical solid dosage form coated with the novel cellulose derivatives of this invention as a film-forming coating material and a method for the coating of the dosage forms. The invention further provides halation preventing layers on photographic films by use of the cellulose derivatives as the vehicle resin and a method for providing the halation preventing layers on the photographic films.

The advantages of the present invention are:

(1) enteric coating films having sufficient flexibility are readily obtained with the cellulose derivatives without the use of a substantial amount of a plasticizer, (2) the solid dosage forms coated with the cellulose derivative are safe from sticking to each other, (3) the cellulose derivatives per se or the coatings produced therewith are chemically and physically stable with the lapse of time against the influence of moisture during storage, (4) the cellulose derivatives can be obtained in a sufficient purity, free of any impurities, since no undesired lumps are formed in the reaction product when subjected to the purification process after completion of the esterification reaction, and (5) the halation preventing layers of the cellulose derivatives formed on photographic films or dry plates are very strong and flexible, highly resistant to hydrolysis, and readily soluble in organic solvents and in aqueous alkaline developing solutions.

DETAILED DESCRIPTION OF THE PREFERRED EMBODIMENTS

Figure 1:
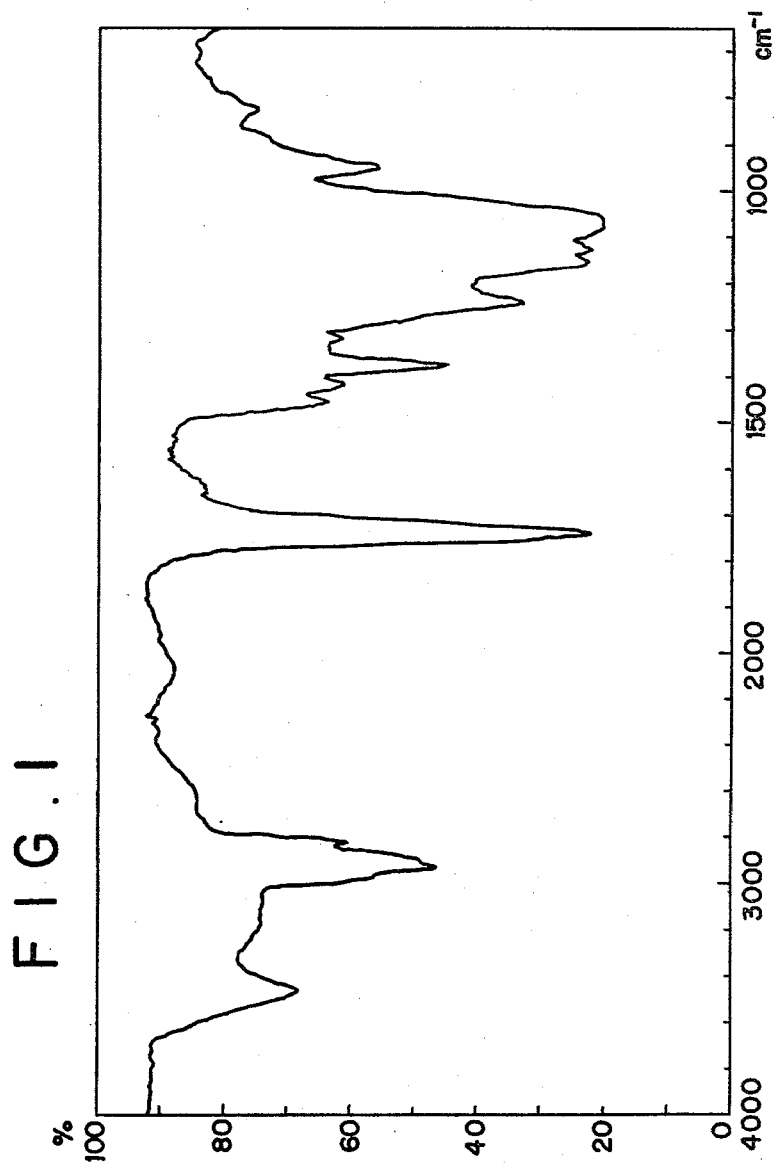
FIGS. 1 to 3 show the infrared absorption spectra of the mixed esters of cellulose ethers with succinyl groups and aliphatic monoacyl groups which were prepared in Examples 1 to 3, respectively, described hereinafter.

The cellulose derivatives is a mixed ester of a cellulose ether with acidic succinyl groups HO—CO—CH$_2$CH$_2$—CO— and aliphatic monoacyl groups represented by the general formula R—CO— where R is an aliphatic monovalent hydrocarbon group, and can be prepared by the reaction of the cellulose ether with succinic anhydride and an anhydride of an aliphatic monocarboxylic acid.

The cellulose ethers suitable as the base material of the inventive compounds are those having alkoxy and-/or hydroxyalkoxy groups in substitution of the hydroxy groups in the glucose units of cellulose forming ether linkages. The cellulose ethers are expressed by the average unit formula $$R^1{}_m R^2{}_n A \qquad (I)$$

in which
- $R^1$ is hydroxyalkyl group, such as hydroxyethyl, hydroxypropyl, or hydroxybutyl,
- $R^2$ is an alkyl group, such as methyl, ethyl, propyl, or butyl,
- A is a glucosic residue of the cellulose structure, and
- m and n are each zero or a positive number corresponding to the degree of substitution with the hydroxyalkyl and alkyl groups, respectively, not equal to zero simultaneously.

Illustrative of the above-defined cellulose ethers are alkylcelluloses, such as methylcellulose, ethylcellulose, and propylcellulose; hydroxyalkylcelluloses, such as hydroxyethylcellulose, hydroxypropylcellulose, and hydroxybutylcellulose; and hydroxyalkylalkylcelluloses, such as hydroxyethylmethylcellulose, hydroxymethylethylcellulose, hydroxypropylmethylcellulose, hydroxypropylethylcellulose, hydroxybutylmethylcellulose, and hydroxybutylethylcellulose; and those having two or more hydroxyalkyl groups, such as hydroxyethylhydroxypropylmethylcellulose.

The cellulose ethers are not limitative in molecular weight and in the degree of substitution with the alkoxy and/or hydroxyalkoxy groups thereof. It is preferred that, in an alkylcellulose or a hydroxyalkylalkylcellulose, the number of the alkyl groups in substitution of the hydroxy groups per glucose unit of the cellulose ether does not exceed 2.5 on an average, since a larger content of the alkyl groups brings about some difficulty in the esterification reaction with the acid anhydrides aforementioned as the esterification agents. It is also preferred that the total degree of substitution in the cellulose ether, i.e. the sum of the numbers m and n in formula (I) above, is at least 0.05 in consideration of easy esterification reaction and in the solubility of the resultant product in organic solvents. Incidentally, it should be noted that larger contents of hydroxyalkyl groups in the cellulose ether have little influence on the reactivity of the cellulose ether in the esterification reaction.

As the succinic anhydride and the anhydrides of aliphatic monocarboxylic acids used for the esterification of the cellulose ethers, commercial grade reagents can generally be used as such. The anhydrides of aliphatic monocarboxylic acids include anhydrides of acetic acid, propionic acid, butyric acid, valeric acid and the like, which preferably have a relatively small number, say, 2 to 4, of carbon atoms in the molecule from the standpoint of industrial availability, inexpensiveness and easiness in handling.

The esterification reaction of the cellulose ether is carried out by either of the following procedures. According to one of the procedures, the cellulose ether is dispersed or dissolved in a carboxylic acid as the reaction medium, such as acetic acid, propionic acid, or butyric acid, followed by reaction with succinic anhydride and an anhydride of the aliphatic monocarboxylic acid in the presence of an alkali carboxylate, such as sodium acetate or potassium acetate, as the esterification catalyst. Alternatively, according to the other procedure, the cellulose ether is reacted with succinic anhydride and an anhydride of the aliphatic monocarboxylic acid as dispersed or dissolved in an organic solvent, such as acetone or dimethylformamide in the presence of a basic catalyst, such as pyridine or α-picoline. The organic solvent used in this case is preferred and possesses a good dissolving power for the cellulose ether at least at a stage where the esterification reaction has proceeded to some extent.

In the former procedure, the cellulose ether as the base material is introduced into the reaction vessel together with about 100 to 2,000 parts by weight of the carboxylic acid as the reaction medium and about 20 to 200 parts by weight of the alkali carboxylate as the catalyst, all being expressed per 100 parts by weight of the cellulose ether, followed by further introduction of predetermined amounts of succinic anhydride and an anhydride of the aliphatic monocarboxylic acid, the resulting mixture being heated at about 60° to 110° C. for a period of time sufficient to complete the reaction, that is, usually from about 2 to 25 hours or longer.

In the latter procedure, 100 parts by weight of the cellulose ether as the starting material is dissolved or dispersed in 50 to 1,000 parts by weight of an organic solvent, such as acetone or dimethylformamide, containing the basic catalyst, such as pyridine and α-picoline, in an amount at least equivalent to the acid anhydrides to be reacted, followed by further addition of predetermined amounts of succinic anhydride and an anhydride of the monocarboxylic acid, the resulting mixture being heated at about 40° to 120° C. for 2 to 120 hours. After completion of the esterification reaction, a large volume of 5–15% sulfuric acid or hydrochloric acid is added to the reaction mixture to precipitate the reaction product, which is then washed with water thoroughly to remove impurities and dried to form a high purity powdery or granular product.

The two anhydrides, i.e., succinic anhydride and aliphatic monocarboxylic acid anhydride, may be introduced into the reaction vessel at the same time or separately one after the other during or after the reaction of either anhydride first introduced. The amount of each anhydride to be introduced is determined depending on the desired degree of esterification to be obtained in the final product, usually being 1.0 to 5.0 times the stoichiometric amounts.

In the above-described procedures for the esterification reaction, the cellulose ether as the starting material is not always soluble in the reaction medium, but can only be dispersed in or swollen by the carboxylic acid or organic solvent, especially, when the degree of substitution in the cellulose ether is relatively small. The esterification reaction can take place even with such a dispersed or swollen cellulose ether and, as the esterification reaction proceeds, the cellulose ether under reaction dissolves in the reaction medium, to finally give a homogeneous solution.

After completion of the esterification reaction, a large volume of water is added to the reaction mixture so that the reaction product is precipitated. The precipitated product is then subjected to thorough washing with water to remove impurities and dried to produce a mixed ester in the powdery or granular form of high purity.

As to the possible mode of the esterification reaction in the cellulose ethers as the base material, there may take place two types of the esterification reaction in the case of hydroxyalkyl- or hydroxyalkylalkyl-celluloses. Namely, the acid anhydrides, i.e. succinic anhydride and an anhydride of the aliphatic monocarboxylic acid can react with the hydroxy groups directly bonded to the glucosic residue of the cellulose or react with the hydroxy groups at the end of the hydroxyalkyl groups $R^1$ in the above formula (I). Unfortunately, no simple method is known for distinguishing one type of the ester groups from the other, and the conventional alkali hydrolysis followed by acid titration of the excess alkali only gives the total of both types of the ester groups.

The average degrees of substitution of the cellulose ether with the acidic succinyl and the aliphatic acyl groups per glucose unit may be controlled by the amounts or concentrations of the anhydrides in the reaction mixture, according to requirements in the properties of the mixed ester as the product. It is usually recommended that the average degree of substitution with acidic succinyl groups and the aliphatic acyl groups is in the range from 0.1 to 1.5 for the acidic succinyl groups or from 0.05 to 2.0 for the aliphatic monoacyl groups in order that the cellulose derivative can dissolve rapidly in alkaline solutions, such as the intestinal juice and photographic developing solutions, and that the coatings or films obtained therewith have sufficient flexibility. In particular, the ranges from 0.15 to 1.0 and from 0.1 to 1.8 for acidic succinyl groups and the aliphatic monoacyl groups, respectively, are preferred when the product is used for the enteric coating of pharmaceutical solid dosage forms.

The coating liquid with the thus prepared mixed ester of a cellulose ether as the film-forming material on solid dosage forms is prepared by dissolving the cellulose derivative in a suitable organic solvent, such as acetone, methylene chloride, ethyl acetate, 1,1,1-trichloroethane, methyl alcohol, ethyl alcohol, isopropyl alcohol, or mixtures thereof in a concentration of about 3 to 20% by weight. It is optional that the coating liquid is admixed with conventional additives, such as coloring agents, flavor improvers, taste improvers, perfumery, plasticizers and the like, according to need.

The pharmaceutical solid dosage forms to be coated with the cellulose derivatives of the present invention include tablets, pills, granules, beads, capsules and the like, and the coating is performed by use of a conventional coating machine, such as a pan coater, drum-type coating machine, or fluidization coating machine, with no specific limitation in operational conditions.

The halation preventing ingredients in the coating liquid for halation preventing layers to be provided with the cellulose derivative as the vehicle resin are known. The procedure for forming the halation preventing layer on the substrate surface of the photographic films or dry plates is also conventional.

For example, the solvents used for the preparation of the coating liquid for the halation preventing layer are exemplified by methyl alcohol, ethyl alcohol, acetone, methylethyl ketone, ethyleneglycol monomethyl ether, ethyleneglycol monoethyl ether, ethyl lactate, toluene, and mixtures of two or more thereof. The halation preventing ingredients are exemplified by carbon black and graphite as well as dyestuffs, such as Spirit Blue CR (Color Index No. 689), Nigrosine Spirit Soluble (Color Index No. 864), alkali Blue B (Color Index No. 704), and Congo Red (Color Index No. 370).

The halation preventing layers in accordance with the present invention are provided on various substrates, for example, of triacetylcellulose, nitrocellulose, polyester resin, polycarbonate resin, and acetylpropionylcellulose. It is optional that the coating liquid for the halation preventing layers contains a small amount of a film-forming agent, such as shellac and a copolymer of unsaturated carboxylic acid monomers, and a solubility improver, such as acetin.

The following examples further illustrate the preparation of the mixed esters of the cellulose ethers and the procedures for coating solid dosage forms and providing the halation preventing layers on the photographic film by the use of the cellulose derivatives of the present invention.

EXAMPLE 1

Into a reaction vessel of 1-liter capacity equipped with a stirrer were introduced 50 g of a hydroxypropylmethylcellulose with degrees of substitution of 0.27 and 1.85 relative to the hydroxypropoxy groups and methoxy groups, respectively, per glucose unit, 250 g of acetic acid, 50 g of sodium acetate, and certain amounts of succinic anhydride and acetic anhydride as indicated in Table I. The mixture was heated at 85° C. with agitation for 3 hours to effect esterification.

After the esterification reaction, about 10 times by volume of water was added to the reaction mixture to allow the reaction product to be precipitated. The precipitated product was filtered, thoroughly washed with water and dried to form products having acidic succinyl groups or acetyl groups by the degree of substitution per glucose unit as indicated in Table I, under Samples 1-5.

It was noted that none of the above reaction products was so sticky to form lumps and difficult in handling during the steps of washing and drying, so that the final products were all obtained in a pure, readily flowable powder form.

The procedures for the determination of the degree of substitution for the acidic succinyl groups on acetyl groups per glucose unit were as follows.

DETERMINATION OF ACIDIC SUCCINYL GROUPS

About 1.0 g of a sample dried at 105° C. for 2 hours was dissolved in 50 ml of a mixed solvent of methylene chloride and methanol (1:1 by volume) and titrated by 0.1 N aqueous sodium hydroxide solution with phenolphthalein as the indicator. The content of the acidic succinyl groups was calculated from the consumption of the sodium hydroxide solution to be converted into the number of the groups per glucose unit.

DETERMINATION OF ACETYL GROUPS

About 0.5 g of a sample dried at 105° C. for 2 hours was dissolved in 50 ml of a mixed solvent of acetone and pyridine (1:1 by volume), followed by the addition of 25 ml of 0.5 N aqueous solution of sodium hydroxide and 25 ml of water. The solution was kept overnight in a closed vessel. The resulting solution was titrated by 0.5 N hydrochloric acid to determine the excessive amount of sodium hydroxide. The content of acetyl groups was calculated from the consumption of the hydrochloric acid with a correction for the above obtained content of acidic succinyl groups.

Further, the solubility test in an organic solvent or a McIlvain buffer solution was carried out for samples 1–5 as the present invention and also for samples 6–8 as the comparative samples. The results are shown in Table I.

In explanation, comparative Example No. 6 was a cellulose acetate phthalate having a degree of substitution of 1.94 or 0.92 relative to the acetyl groups and phthaloyl groups, respectively, per glucose unit; Example No. 7 was a hydroxypropylmethylcellulose phthalate having a degree of substitution of 0.22, 1.88 or 0.68 relative to the hydroxypropoxy, methoxy, and phthaloyl groups, respectively, per glucose unit; and Example No. 8 was a hydroxypropylmethylcellulose succinate having a degree of substitution of 0.22, 1.88 or 0.76 relative to the hydroxypropoxy, methoxy, and succinoyl groups, respectively, per glucose unit.

The solubility test in an organic solvent was a visual examination undertaken by periodically shaking 0.5 g of the sample dispersed in 10 ml of the solvent in a test tube, to find whether dissolved or not. The solubility test in the McIlvain buffer solution was conducted in accordance with the Japanese Pharmacopoeia, 9th Revision, by placing a test piece 10×10 mm wide and about 0.1 mm thick of the cellulose derivative in a disintegration tester for tablets and passing the McIlvain buffer solution having a pH value of 4.6, 5.0, 5.6, 6.0 or 7.0 at 37°±2° C., to determine the time required for the test piece film to be completely dissolved or disappear.

Furthermore, samples 2, 4 and 5 and comparative samples 6–8 were subjected to the stability test against hydrolysis and determination of the physical properties of the coatings or films formed therewith in the manner set forth below.

The stability test was conducted by keeping the sample for 6 or 12 days in a sealed tube at 60° C. with a relative humidity of 100%, then analyzing for aliphatic monocarboxylic acid freed from the sample and overall free acids, and accordingly calculating the amount of the free acid other than the aliphatic monocarboxylic acid.

The procedures for the analysis were as follows.

(a) The sample was subjected to extraction in a Soxhlet extractor with diethyl ether as the solvent for 5 hours. The extract solution was analyzed by gas chromatography for the content of the aliphatic monocarboxylic acid. The results were recorded after correction for the value of the parallel blank test in % by weight based on the amount of the starting sample.

(b) Separately, the sample was dissolved in a 1:1 mixed solvent of methylene chloride and methyl alcohol and, after dilution with n-hexane, the solution was extracted with water. The aqueous extract was titrated with a 0.1 normal aqueous solution of sodium hydroxide, to give the total amount of the free acids.

(c) The difference between the thus determine total amount of the free acids and the amount of the aliphatic monocarboxylic acid obtained in a) above was recorded as the amount of the free acids other than the aliphatic monocarboxylic acid after correction for the value of the parallel blank test.

The physical properties were determined with respect to tensile strength, ultimate elongation and stickiness for each cellulose derivative sample formed into a film about 0.1 mm thick by casting the solution in a mixed solvent of methylene chloride and methyl alcohol on a glass plate. The tests for tensile strength and ultimate elongation were carried out, using a Tensilon tester of Model UTM-III (manufactured by Toyo Baldwin Co.). The test for stickiness was carried out by press-contacting two pieces of the film sample each 20×20 mm wide under a load of 1 $kg/cm^2$ at 70° C. for 2 hours and, after removal of the load and cooling to room temperature, examining the bonding of the film pieces.

TABLE I

| Sample No. | | Present Invention | | | | | Comparative Samples | | |
|---|---|---|---|---|---|---|---|---|---|
| | | 1 | 2 | 3 | 4 | 5 | 6 | 7 | 8 |
| Succinyl anhydride, g | | 60 | 40 | 25 | 20 | 15 | — | — | — |
| Acetic anhydride, g | | 25 | 25 | 50 | 60 | 80 | — | — | — |
| Acidic succinyl groups per glucose unit | | 0.75 | 0.70 | 0.46 | 0.43 | 0.25 | — | — | — |
| Acetyl groups per glucose unit | | 0.11 | 0.26 | 0.36 | 0.43 | 0.57 | — | — | — |
| Solubility in organic solvent | Acetone | Yes | Yes | Yes | Yes | Yes | Yes | Yes | Yes |
| | Methyl alcohol | Yes | Yes | Yes | Yes | Yes | No | No | Yes |
| | Toluene | No | No | No | No | * | No | No | No |
| | Methylene chloride + Methyl alcohol (1:1) | Yes | Yes | Yes | Yes | Yes | Yes | Yes | Yes |
| Solubility in McIlvain buffer solution minutes | pH 4.6 | ** | ** | ** | ** | ** | ** | ** | ** |
| | pH 5.0 | 14–18 | 15–19 | ** | ** | ** | ** | ** | 18–22 |
| | pH 5.6 | 6–8 | 6–8 | 10–15 | 9–11 | ** | 80–90 | 17–20 | 8–10 |
| | pH 6.0 | 5–7 | 6–8 | 7–9 | 7–9 | 20–25 | 13–17 | 8–10 | 4–6 |
| | pH 7.0 | 3–6 | 5–7 | 5–7 | — | 7–12 | — | — | — |

*Swelling took place.
**The test piece was not dissolved.

The results of the above stability tests and determination of the physical properties are set out in Table II.

TABLE II

| | Sample No. | | Present Invention | | | Comparative Sample | | |
|---|---|---|---|---|---|---|---|---|
| | | | 2 | 4 | 5 | 6 | 7 | 8 |
| Stability as expressed by free acids % by weight | After 6 days at 60° C. 100% R. H. | Succinic acid | 2.0 | 1.1 | 0.4 | — | — | 2.7 |
| | | Phthalic acid | — | — | — | 9.3 | 3.1 | — |
| | | Acetic acid | 0.1 | 0.5 | 0.4 | 7.0 | — | — |
| | After 12 days at 60° C. 100% R. H. | Succinic acid | 2.2 | 1.6 | 0.5 | — | — | 3.2 |
| | | Phthalic acid | — | — | — | 13.2 | 3.4 | — |
| | | Acetic acid | 0.2 | 0.6 | 0.7 | 11.0 | — | — |
| Physical properties | Tensile strength, kg/cm$^2$ | | 400–500 | 440–600 | 400–550 | 360–570 | 430–550 | 400–520 |
| | Ultimate elongation, % | | 7.5–10.0 | 7.5–10.0 | 7.5–10.0 | 2.5–7.5 | 0–2.5 | 7.5–12.5 |
| | Stickiness | | No | No | No | No | No | Yes |

Besides the above, a film formed with the mixed ester product of Sample 3 was tested for infrared absorption spectrum and shown by way of FIG. 1.

EXAMPLE 2

The esterification reaction was undertaken in the same manner as in Example 1 with 50 g of a hydroxylpropylcellulose having a degree of substitution 2.40 relative to the hydroxypropyl groups per glucose unit, 40 g of succinic anhydride and 40 g of acetic anhydride, to obtain a mixed ester product having a degree of substitution 1.10 or 0.70 relative to the acidic succinyl groups and acetyl groups, respectively, per glucose unit.

The mixed ester product thus obtained (Sample No. 9) was soluble in acetone, methyl alcohol and a 1:1 mixed solvent of methylene chloride and methyl alcohol, and also in McIlvain buffer solutions having a pH value of 5.0 or higher.

Figure 2:
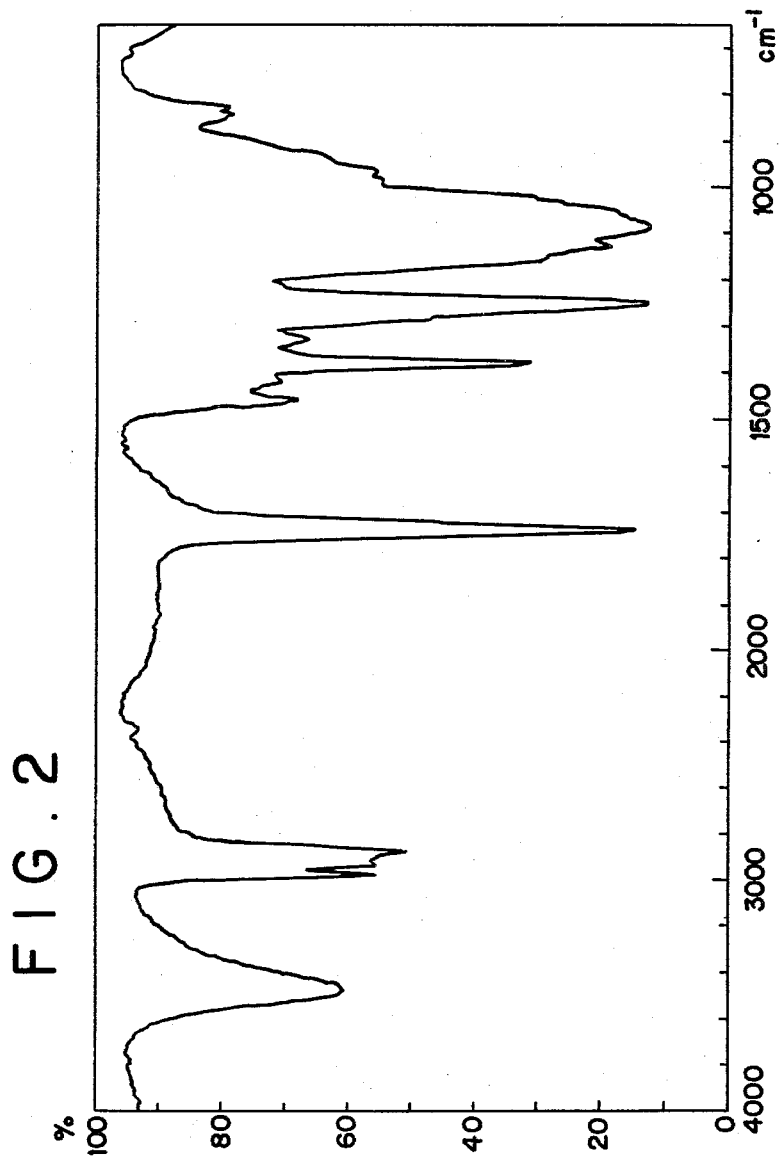

The infrared absorption spectrum of the film formed with the mixed ester product is shown by way of FIG. 2.

EXAMPLE 3

The esterification reaction was undertaken with 50 g of a methylcellulose having a degree of substitution 1.90 per glucose unit, 40 g of succinic anhydride and 30 g of propionic anhydride dispersed in 250 g of propionic acid as the reaction medium containing 50 g of potassium acetate by heating at 85° C. for 5 hours. The resultant mixed ester product had a degree of substitution of 0.68 or 0.22 relative to the acidic succinyl groups and the propionyl groups, respectively, per glucose unit.

The mixed ester product thus obtained (Sample No. 10) was soluble in acetone and a 1:1 mixed solvent of methylene chloride and methyl alcohol, and also in McIlvain buffer solutions having a pH value of 5.0 or higher.

Figure 3:
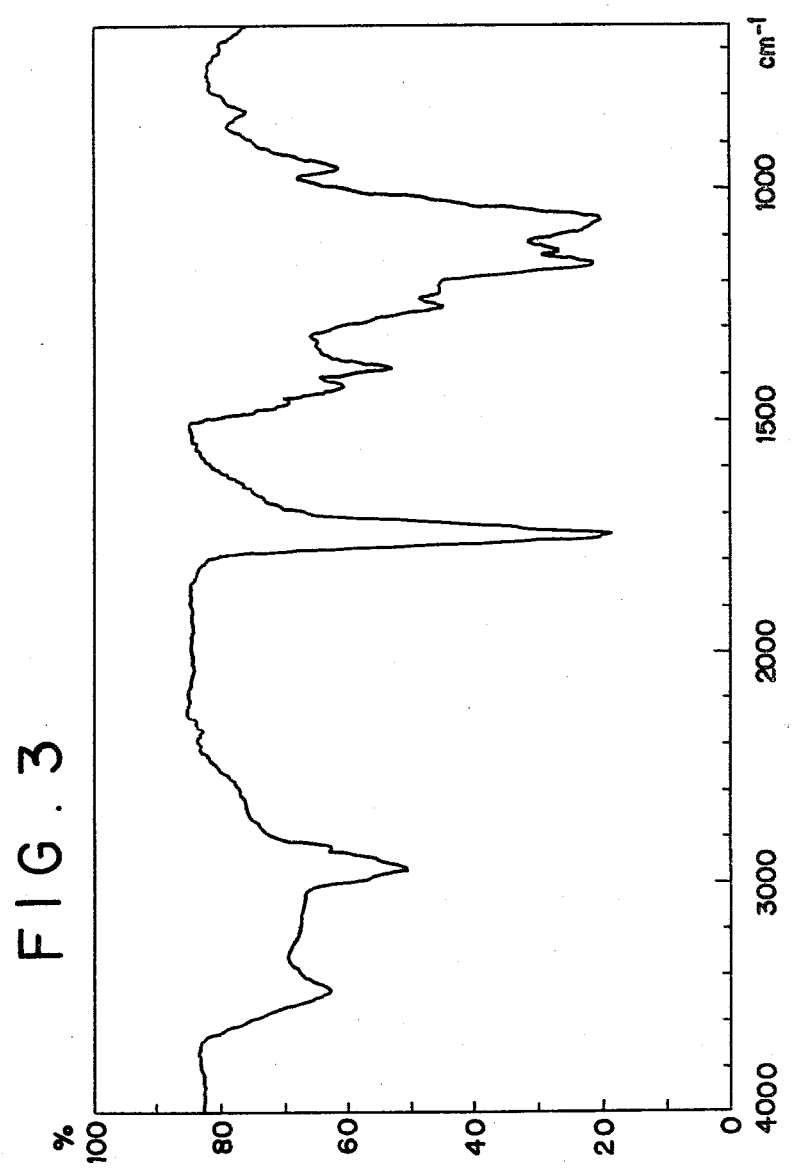

The infrared absorption spectrum of the film formed with the mixed ester product is shown by way of FIG. 3.

EXAMPLE 4

The esterification reaction was undertaken in the same manner as in Example 1 with 50 g of a hydroxyethylethylcellulose having a degree of substitution of 0.72 or 0.85 relative to the hydroxyethoxy groups and the ethoxy groups, respectively, per glucose unit, 40 g of succinic anhydride and 30 g of n-butyric anhydride. The resultant mixed ester product had a degree of substitution of 0.62 or 0.19 relative to the acidic succinyl groups and the n-butyryl groups, respectively, per glucose unit.

The mixed ester product thus obtained (Sample No. 11) was soluble in acetone, methyl alcohol and a 1:1 mixed solvent of methylene chloride and methyl alcohol, and also in McIlvain buffer solutions having a pH value of 5.0 or higher.

EXAMPLE 5

Three kinds of mixed ester cellulose ether derivatives, Samples No. 12 to No. 14, were prepared in the same manner as in Example 1 except that the starting cellulose ether was either one of hydroxypropylcellulose having a degree of substitution of 3.0 relative to the hydroxypropoxy groups per glucose unit (in Sample No. 12), hydroxybutylmethylcellulose having a degree of substitution of 0.10 or 1.80 relative to the hydroxybutoxy groups and methoxy groups, respectively, per glucose unit (in Sample No. 13), or hydroxyethylhydroxypropylcellulose having a degree of substitution of 2.5 or 0.32 relative to the hydroxyethoxy groups and hydroxypropoxy groups, respectively, per glucose unit (in Sample No. 14). The amounts of the acid anhydrides as well as the kind of the anhydride of the monocarboxylic acid used were varied as indicated in Table III. The degree of substitution in the mixed ester products thus obtained are summarized in the same table.

The mixed ester products were tested for stability and ultimate elongation in the same manner as in Example 1 along with two comparative samples No. 15 and No. 16. The results are set out in Table III.

Sample 15 was a hydroxypropylmethylcellulose hexahydrophthalate having a degree of substitution of 0.22, 1.84 relative to the hydroxypropoxy, methoxy, and hexahydrophthaloyl groups, respectively, per glucose unit. Sample 16 was a hydroxypropylcellulose succinate having a degree of substitution of 3.0 or 1.33 relative to the hydroxypropoxy and succinoyl groups, respectively, per glucose unit.

TABLE III

| | Present Invention | | | Comparative Sample | |
|---|---|---|---|---|---|
| Sample No. | 12 | 13 | 14 | 15 | 16 |
| Succinic anhydride, g | 10 | 17.5 | 15 | — | — |
| Aliphatic monocarboxylic acid anhydride, g | Acetic (50) | Butyric (120) | propionic (100) | — | — |
| Acidic succinyl groups per glucose unit | 0.20 | 0.23 | 0.30 | — | — |

TABLE III-continued

| Sample No. | | | Present Invention | | | Comparative Sample | |
|---|---|---|---|---|---|---|---|
| | | | 12 | 13 | 14 | 15 | 16 |
| Aliphatic monoacyl groups per glucose unit | | | 0.86 | 0.54 | 0.85 | — | — |
| Stability as expressed by free acids, % by weight | After 6 days at 60° C., 100% R.H. | Succinic acid | 0.1 | 0.3 | 0.4 | — | 3.4 |
| | | Hexahydrophthalic acid | — | — | — | 1.9 | — |
| | | Aliphatic mono-carboxylic acid | 0.3 | 0.4 | 0.7 | — | — |
| | After 12 days at 60° C., 100% R.H. | Succinic acid | 0.2 | 0.4 | 0.7 | — | 5.6 |
| | | Hexahydrophthalic acid | — | — | — | 2.3 | — |
| | | Aliphatic mono-carboxylic acid | 0.6 | 0.6 | 1.0 | — | — |
| Ultimate elongation of film, % | | | 15–20 | 7.5–10.0 | 7.5–10.0 | 2.5–5.0 | 60–70 |

EXAMPLE 6

Into a reaction vessel of 1-liter capacity equipped with a stirrer were introduced 50 g of the same hydroxypropylmethylcellulose as used in Example 1, 150 g of acetone, and certain amounts of pyridine, succinic anhydride and acetic anhydride as indicated in Table IV as Sample No. 17 or 18. The mixture was subjected to reaction at the boiling point of acetone for 15 hours.

The reaction mixtures thus obtained were mixed with about 10 times by volume 12% hydrochloric acid, to precipitate the reaction product, which was then thoroughly washed with water and dried, to give the mixed ester product with a degree of substitution as indicated in the table relative to the acidic succinyl groups and acetyl groups.

Each product was soluble in acetone, methyl alcohol or a 1:1 mixed solvent of methylene chloride and methyl alcohol, and also in McIlvain buffer solutions having a pH value of 5.0 or higher when it was Sample No. 17 or 5.5 or higher when it was Sample 18.

TABLE IV

| Sample No. | 17 | 18 |
|---|---|---|
| Pyridine, g | 70 | 80 |
| Succinic anhydride, g | 45 | 30 |
| Acetic anhydride, g | 30 | 50 |
| Acidic succinyl groups per glucose unit | 0.68 | 0.45 |
| Aceteyl groups per glucose unit | 0.22 | 0.35 |

EXAMPLE 7

A 3:7 mixture of starch and lactose was shaped into tablets each weighing 250 mg, and the tablets were coated by the spraying method with a 10% by weight acetone solution of a mixed ester product of Sample No. 4, 9, 10 or 11 in a coating amount of 25 mg per tablet.

The thus coated tablets were subjected to the disintegration test in accordance with the Japanese Pharmacopoeia, 9th Revision, with first testing solution of pH 1.2 and a second testing solution of pH 7.5. The disintegration time of the coated tablets in the first testing solution was 2 hours or longer for all of the mixed ester products as the coating material, and that in the second testing solution was 5–8 minutes, 7–10 minutes, 7–10 minutes and 7–12 minutes for the above 4 samples, respectively.

EXAMPLE 8

Coating liquids were prepared for providing halation preventing layers on photographic films with the following formulations.

| | Parts by weight |
|---|---|
| Formulation A: | |
| Sample No. 12 | 3.0 |
| Spirit Blue (C. I. No. 689) | 1.0 |
| Carbon Black | 1.0 |
| Ethyl alcohol | 95.0 |
| Formulation B: | |
| Sample No. 5 | 1.0 |
| A copolymer of methacrylic acid and methyl methacrylate (3:7 by moles) | 1.0 |
| Carbon black | 1.2 |
| Acetone | 40.0 |
| Ethyl alcohol | 26.0 |
| Ethyleneglycol monomethyl ether | 30.8 |
| Formulation C: | |
| Sample No. 13 | 2.2 |
| Carbon Black | 1.0 |
| Acetone | 65.0 |
| Methyl alcohol | 16.0 |
| Ethyleneglycol monomethyl ether | 15.8 |
| Formulation D: | |
| Sample No. 14 | 2.2 |
| Carbon black | 1.0 |
| Acetone | 65.0 |
| Methyl alcohol | 16.0 |
| Ethyleneglycol monomethyl ether | 15.8 |

Each coating liquid thus prepared was applied uniformly on the surface of a triacetylcellulose film base opposite to the surface on which a layer of silver halide/gelation emulsion is provided, and then dried. The halation preventing layer thus formed was 3 μm thick.

The photographic film having the halation preventing layer was kept rolled in the atmosphere at 40° C. with a relative humidity of 67% for 2 months, to find that the emulsion layer was not adversely affected and that the halation preventing layer could be readily removed by treatment with an alkaline photographic developing solution.

What is claimed is:

1. A method of preparing a mixed ester selected from the class consisting of alkylcellulose, hydroxyalkylcellulose and hydroxyalkylalkylcellulose esterified with acidic succinyl groups expressed by the formula HO—CO—CH$_2$CH$_2$CO— and acyl groups represented by the general formula R—CO— where R is an aliphatic monovalent hydrocarbon group, which comprises esterifying a cellulose ether represented by the formula $R^1{}_m R^2{}_n A$ where $R^1$ is a hydroxyalkyl group, $R^2$ is an alkyl group, A is a glucosic residue and m and n are each zero or a positive number not equal to zero simultaneously, with succinic anhydride and an anhydride of an aliphatic monocarboxylic acid.

2. The method as claimed in claim 1, wherein the esterification is carried out in an aliphatic monocarboxylic acid as the reaction medium and in the presence of a carboxylate of an alkali metal as the catalyst.

3. The method as claimed in claim 1, wherein the esterification is carried out in acetone or dimethylformamide as the reaction medium and in the presence of a basic catalyst.

4. The method as claimed in claim 1, wherein m and n have values such that m+n is at least 0.05.

5. The method as claimed in claim 1, wherein the cellulose ether is a hydroxypropylmethylcellulose.

6. The method as claimed in claim 1, wherein the cellulose ether is a hydroxypropylcellulose.

7. The method as claimed in claim 1, wherein the cellulose ether is a hydroxyethylcellulose.

8. The method as claimed in claim 1, wherein the cellulose ether is a methylcellulose.

9. Mixed ester of a cellulose ether prepared according to the process defined in claim 1.

10. Mixed ester according to claim 9, wherein the average degree of substitution with the acidic succinyl groups or the acyl groups represented by the general formula R—CO— is from 0.1 to 1.5 or from 0.05 to 2.0, respectively, per glucose unit of the cellulose structure.

11. A method for providing enterosoluble coatings on a solid dosage form which comprises applying a solution of a mixed ester of a cellulose ether in an organic solvent to the solid dosage form and drying, said mixed ester having been formed from esterifying alkylcellulose, hydroxyalkylcellulose, or hydroxyalkylalkylcellulose with acidic succinyl groups expressed by the formula HO—CO—CH$_2$—CH$_2$CO—, and acyl groups represented by the general formula R—CO— where R is an aliphatic monovalent hydrocarbon group.

12. A solid dosage form with an entersoluble coating layer characterized in that the coating layer comprises a mixed ester of a cellulose ether from esterifying alkylcellulose, hydroxyalkylcellulose, or hydroxyalkylalkylcellulose with acidic succinyl groups expressed by the formula HO—CO—CH$_2$—CH$_2$CO—, and acryl groups represented by the general formula R—CO— where R is an aliphatic monovalent hydrocargon group.

13. A solid dosage form according to claim 12 wherein said mixed ester is derived from a hydroxypropylmethylcellulose.

14. A solid dosage form according to claim 12 wherein said mixed ester is derived from a hydroxypropylcellulose.

15. A solid dosage form according to claim 12 wherein said mixed ester is derived from a hydroxyethylcellulose.

16. A solid dosage form according to claim 12 wherein said mixed ester is derived from a methylcellulose.

17. A method for providing a halation preventing layer on the surface of a photographic film which comprises applying a solution of the mixed ester of a cellulose ether in an organic solvent to the surface of the photographic film and drying, said mixed ester having been formed from esterifying alkylcellulose, hydroxyalkylcellulose, or hydroxyalkylalkylcellulose with acidic succinyl groups expressed by the formula HO—CO—CH$_2$—CH$_2$CO—, and acyl groups represented by the general formula R—CO— where R is an aliphatic monovalent hydrocarbon group.

18. A photographic film provided with a halation preventing layer on one of its surface which comprises a halation preventing layer including the mixed ester of a cellulose ether as a vehicle resin, said mixed ester being formed from esterifying alkylcellulose, hydroxyalkylcellulose, or hydroxyalkylalkylcellulose with acidic succinyl groups expressed by the formula HO—CO—CH$_2$—CH$_2$CO—, and acyl groups represented by the general formula R—C— where R is an aliphatic monovalent hydrocarbon group.

* * * * *